(12) United States Patent
Cooke et al.

(10) Patent No.: US 6,723,993 B2
(45) Date of Patent: Apr. 20, 2004

(54) EVENT LOCALIZATION AND FALL-OFF CORRECTION BY DISTANCE-DEPENDENT WEIGHTING

(75) Inventors: Steven E. Cooke, Garfield Heights, OH (US); John F. Vesel, Kirtland, OH (US); Frank P. DiFilippo, Strongsville, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 10/298,027

(22) Filed: Nov. 15, 2002

(65) Prior Publication Data

US 2003/0116713 A1 Jun. 26, 2003

Related U.S. Application Data

(62) Division of application No. 09/846,013, filed on Apr. 30, 2001, now Pat. No. 6,603,125.
(60) Provisional application No. 60/209,032, filed on Jun. 2, 2000.

(51) Int. Cl.⁷ ................................................ G01T 1/20
(52) U.S. Cl. ............. 250/369; 250/363.07; 250/362.03; 250/362.02; 250/366
(58) Field of Search .............................. 250/369, 363.07, 250/363.03, 370.1, 370.11, 370.09, 366, 363.02

(56) References Cited

U.S. PATENT DOCUMENTS

| | | | | |
|---|---|---|---|---|
| 5,293,044 A | | 3/1994 | Klingenbeck-Regn | 250/369 |
| 5,345,082 A | | 9/1994 | Engdahl et al. | 250/363.07 |
| 5,491,342 A | | 2/1996 | Lim et al. | 250/363.09 |
| 5,545,898 A | * | 8/1996 | Gagnon et al. | 250/369 |
| 5,576,547 A | | 11/1996 | Ferreira et al. | 250/369 |
| 6,198,104 B1 | * | 3/2001 | Geagan et al. | 250/363.04 |
| 6,252,232 B1 | * | 6/2001 | McDaniel et al. | 250/369 |
| 6,291,825 B1 | * | 9/2001 | Scharf et al. | 250/369 |
| 6,310,349 B1 | * | 10/2001 | Wong et al. | 250/363.09 |
| 6,348,692 B1 | | 2/2002 | Chapuis et al. | 250/369 |
| 6,525,323 B1 | * | 2/2003 | Vesel et al. | 250/369 |

FOREIGN PATENT DOCUMENTS

FR  2757956  7/1998

OTHER PUBLICATIONS

Geagan, et al. "Correction of Distortions in a Discontinuous Image", Nuclear Instr. & Methods in Physics Research A 353 (1994) 379–383.

* cited by examiner

Primary Examiner—Albert Gagliardi
(74) Attorney, Agent, or Firm—Fay, Sharpe, Fagan, Minnich & Mckee, LLP

(57) ABSTRACT

A nuclear camera system includes a detector (12) for receiving radiation from a subject (14) in an exam region (16). The detector (12) includes a scintillation crystal (20) that converts radiation events into flashes of light. An array of sensors (22) is arranged to receive the light flashes from the scintillation crystal (20). Each of the photomultiplier sensors (22) generates a respective sensor output value in response to each received light flash. A processor (26) determines when each of the radiation events is detected. At least one of an initial position and an energy of each of the detected radiation events is determined in accordance with respective distances ($d_1 \ldots d_{19}$) from a position of the detected event to the sensors (22). An image representation is generated from the initial positions and energies.

17 Claims, 9 Drawing Sheets

EVENT LOCALIZATION AND FALL-OFF CORRECTION BY DISTANCE-DEPENDENT WEIGHTING

This application is a divisional of U.S. patent application Ser. No. 09/846,013, filed Apr. 30, 2001, now U.S. Patent No. 6,603,125, and claims the benefit of U.S. Provisional Application No. 60/209,032, filed Jun. 2, 2000.

BACKGROUND OF THE INVENTION

The present invention relates to the art of nuclear medicine and diagnostic imaging. It finds particular application in localizing a scintillation event in a gamma camera having a number of photomultipliers arranged over a camera surface. It is to be appreciated that the present invention may be used in conjunction with positron emission tomography ("PET"), single photon emission computed tomography ("SPECT"), whole body nuclear scans, transmission imaging, other diagnostic modes and/or other like applications. Those skilled in the art will also appreciate applicability of the present invention to other applications where a plurality of pulses tend to overlap, or "pile-up" and obscure one another.

Diagnostic nuclear imaging is used to study a radio nuclide distribution in a subject. Typically, one or more radiopharmaceutical or radioisotopes are injected into a subject. The radiopharmaceutical are commonly injected into the subject's bloodstream for imaging the circulatory system or for imaging specific organs that absorb the injected radiopharmaceutical. A gamma or scintillation camera detector head is placed adjacent to a surface of the subject to monitor and record emitted radiation. Each detector typically includes an array of photomultiplier tubes facing a large scintillation crystal. Each received radiation event generates a corresponding flash of light (scintillation) that is seen by the closest photomultiplier tubes. Each photomultiplier tube that sees an event generates a corresponding analog pulse. Respective amplitudes of the pulses are generally proportional to the distance of each tube from the flash.

A fundamental function of a scintillation camera is event estimation, which is the determination of energy and position of the location of an interacting gamma or other radiation ray based on the detected electronic signals. A conventional method for event positioning is known as the Anger method, which sums and weights signals seen by tubes after the occurrence of an event. The Anger method for event positioning is based on a simple first moment calculation. More specifically, the energy is typically measured as the sum of all the photomultiplier tube signals, and the position is typically measured as the "center of mass" of the photomultiplier tube signals.

Several methods have been used for implementing the center of mass calculation. With fully analog cameras, all such calculations (e.g., summing, weighting, dividing) are done using analog circuits. With hybrid analog/digital cameras, the summing and weighting are done using analog circuits, but the summed values are digitized and the final calculation of position is done digitally. With "fully digital" cameras, the tube signals will be digitized individually. In any event, because the fall-off curve of the photomultipliers is not linear as assumed by the Anger method, the image created has non-linearity errors.

One important consideration is the location of the event estimation. The scintillation light pulse is mostly contained within a small subset of the tubes on a detector. For example, over 90% of a total signal is typically detected in seven (7) out of a total number of tubes, typically on the order of 50 or 60. However, imaging based only on the seven (7) closest tubes, known as clustering, has poor resolution and causes uniformity artifacts. Furthermore, because the photomultiplier tubes have non-linear outputs, the scintillation events are artificially shifted toward the center of the nearest photomultiplier tube.

For a given detector geometry, the fall-off curve varies with a depth that a gamma photon interacts in the crystal. Different energy photons have varying interaction depth probabilities that are more pronounced in thicker crystals, which are typically used in combination with PET/SPECT cameras.

Therefore, separate linearity or flood correction tables are created and used for each energy in order to correct for the uniformity artifact. Fall-off curves are acquired using a labor intensive method of moving a point source a small amount (e.g., 2 mm) roughly 30–40 times for each tube. The individual tube's output is acquired at each location, the mean value of the tube's output is found, and a curve of tube output versus distance from the location of the point source is generated.

A disadvantage of generating a fall-off curve using a point source is the large amount of time required to move the source position. This method is also prone to errors in positioning the source accurately on the detector. It is also usually only done in one or two directions Therefore, the assumption is made that the fall-off curve is exactly symmetric. Regenerating the fall-off curve for a different energy requires that the process be repeated again. Likewise, generating the fall-off curve for a different tube requires the process be repeated again. Therefore, the assumption is usually made that the fall-off curve is invariant across different detectors or photomultiplier tubes.

Generating the linearity correction tables typically involves using a lead mask that contains many small holes to restrict the incident location of radiation on the crystal surface. The holes represent the true location of the incident photons that interact in the detector crystal. This information is used to generate a table that consists of x and y deltas that when added to the x and y estimate, respectively, are used to generate a corrected position estimate that more accurately reflects the true position. A disadvantage is that new tables must be generated for each energy that is to be imaged, thereby increasing the calibration time. Another disadvantage is that the calibration mask has a limited number of holes, since each must be resolved individually, thereby limiting the accuracy of the correction. It is also increasingly more expensive and difficult to calibrate for higher energy photons since the thickness of the lead mask must increase in order to have sufficient absorption in non-hole areas.

Another prior art method uses separate flood uniformity correction tables for each energy. A disadvantage is that new tables must be generated for each energy that is to be imaged, which increases calibration time. Flood correction has the disadvantage of creating noise in the image, since the method is based on either adding or removing counts unevenly throughout the pixel matrix. This method is also sensitive to drift in either the photomultiplier tubes or electronics.

Another prior art method reduces the output from the closest tube. For example, an opaque dot is sometimes painted over the center of each photomultiplier tube. The sensitivity can also be reduced electronically. Unfortunately, the closest photomultiplier tube typically has the best noise statistics. Reducing its sensitivity to the event causes a resolution loss.

Similarly, excluding the outlying tubes reduces the noise in the determined values of energy and position. The most common way of excluding signals from outlying tubes includes imposing a threshold, such that tube signals below a set value are either ignored in the calculation or are adjusted by a threshold value. This method works reasonably well in excluding excess noise. However, the method fails if stray signals exist above the threshold value. Stray signals may exist at high-counting rates, when events occur nearly simultaneously in the crystal. When two events occur substantially simultaneously, their "center-of-mass" is midway between the two—where no event actually occurred. Nearly simultaneously occurring events may result in pulse-pile-up in the energy spectrum and mispositioning of events. This behavior is especially detrimental in coincidence imaging, where high-count rates are necessary.

Thus, it is desirable to improve localization in event estimation. With a fully digital detector, both the intensity and the location of each tube signal are known. It is, therefore, possible to calculate the energy and position based primarily on the tube signals close to an individual event. One current method for event localization is seven (7) tube clustering in which a cluster of seven (7) tubes is selected for each event. These tubes include the tube with maximum amplitude, along with that tube's six (6) closest neighbors. This method is an effective method for limiting the spatial extent of the calculation. However, the main drawback of this method is the resulting discontinuity.

Discontinuity arises when the detected positions for events from a uniform flood source form an array of zones around each possible cluster. Elaborate correction schemes (see e.g., Geagan, Chase, and Muehllehner, Nucl. Instr. Meth. Phys. Res A 353, 379–383 (1994)) are needed to "stitch" together these overlapping zones to form a single, continuous image. However, this correction is sensitive to electronic shifts, which often arise in high-count situations, causing seam artifacts in the camera response.

The present invention provides a new and improved apparatus and method which overcomes the above-referenced problems and others.

SUMMARY OF THE INVENTION

A nuclear camera system includes a detector for receiving radiation from a subject in an exam region. The detector head includes a scintillation crystal, which converts radiation events into flashes of light, and an array of sensors, which are arranged to receive the light flashes from the scintillation crystal. Each of the sensors generates a respective sensor output value in response to each received light flash. A processor determines when each of the radiation events is detected. At least one of an initial digital position and an energy of each of the detected radiation events is determined in accordance with respective distances from a position of the detected event to the sensors. An image representation is generated from the digital positions.

In accordance with one aspect of the invention, each of the sensors is electrically connected to at least one of a plurality of analog-to-digital converters for converting the sensor output values from analog values to respective series of digital sensor output values.

In accordance with another aspect of the invention, the processor weights the sensor output values with weighting values for determining corrected positions of the events. The weighting values are determined in accordance with the respective distances from the position of each event to each of the sensors that detects the event.

In accordance with a more limited aspect of the invention, the processor determines a subsequent set of weighting values as a function of the corrected positions and energies of the events.

In accordance with another aspect of the invention, the processor generates the weighting values for each of the distances as a function of a desired response curve and an input response curve.

In accordance with a more limited aspect of the invention, the processor generates the weighting values as a function of the energy being imaged.

In accordance with an even more limited aspect of the invention, the processor generates energy ratio curves representing respective relationships between a plurality of the energies being imaged. The processor generates an energy scaling curve representing a relationship between the plurality of energies being imaged and respective scaling factors. Also, the processor generates the weighting values as a function of one of the scaling factors.

In accordance with another aspect of the invention, a look-up table is accessed by the processor for storing the weighting values.

In accordance with a more limited aspect of the invention, the look-up table is multi-dimensional and indexed as a function of at least one of time, temperature, count-rate, depth of interaction, and event energy.

In accordance with another aspect of the invention, the processor analyzes the sensor output values for detecting a start of the event.

In accordance with a more limited aspect of the invention, the processor analyzes the sensor output values for detecting a previous event. Any sensor output values associated with the previous event are excluded from calculations of an initial position and an energy of a next detected event.

In accordance with another aspect of the invention, in response to the processor detecting a next event after an integration period of the event begins, during which the position of the detection event is determined, the sensor values associated with the sensors of the next event are nulled from calculations of the initial position and the energy of the event.

In accordance with another aspect of the invention, a second detector disposed across an imaging region from the first detector. A coincidence detector is connected with the first and second detectors for detecting concurrent events on both detectors. A reconstruction processor determines rays through the imaging region between concurrent events and reconstructs the rays into an output image representation.

In accordance with another aspect of the invention, an angular position detector determines an angular position of the detector around an imaging region. A reconstruction processor is connected with the detector and the angular position detector for reconstructing a volumetric image representation from the corrected positions of the events on the detector and the angular position of the detector during each event.

In accordance with another aspect of the invention, the sensors include photomultiplier tubes.

One advantage of the present invention resides in its high linearity. Therefore, linearity and uniformity corrections are reduced.

Another advantage resides in improved accuracy in event positioning, even in high count and pile-up situations.

Another advantage is that local centroiding is continuous and seamless.

Another advantage resides in more accurate estimation of events.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
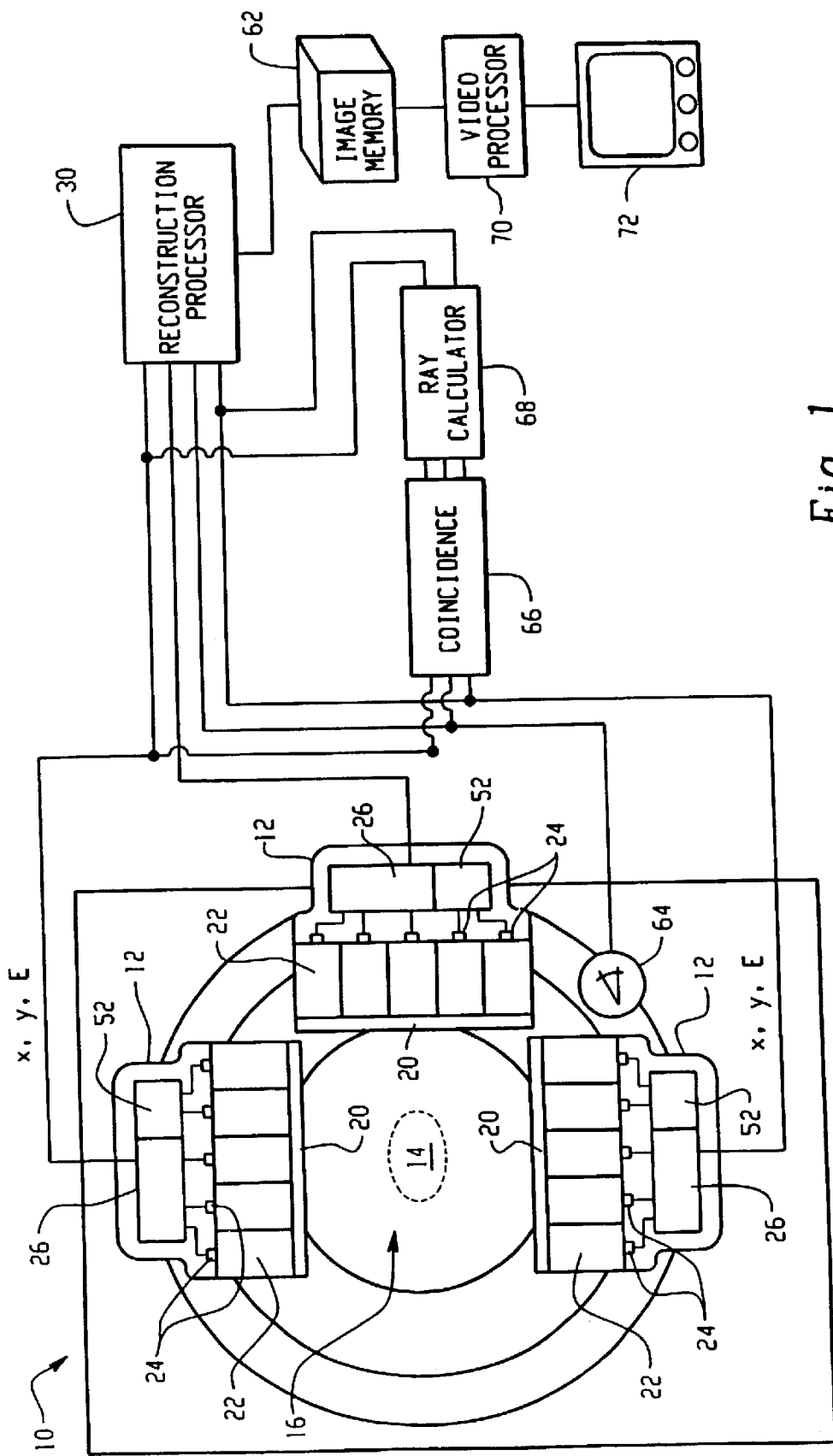
FIG. 1 is a diagrammatic illustration of a nuclear camera system according to the present invention.

With reference to FIG. 1, a nuclear camera system 10 includes a plurality of detectors heads ("detectors") 12 mounted for movement around a subject 14 in an examination region 16. Each of the detectors 12 includes a scintillation crystal 20 that converts a radiation event into a flash of light energy or scintillation. An array of sensors 22, e.g. 59 sensors, is arranged to receive the light flashes from the scintillation crystal. In the preferred embodiment, the sensors include photomultiplier tubes. However, other sensors are also contemplated.

Figure 5:
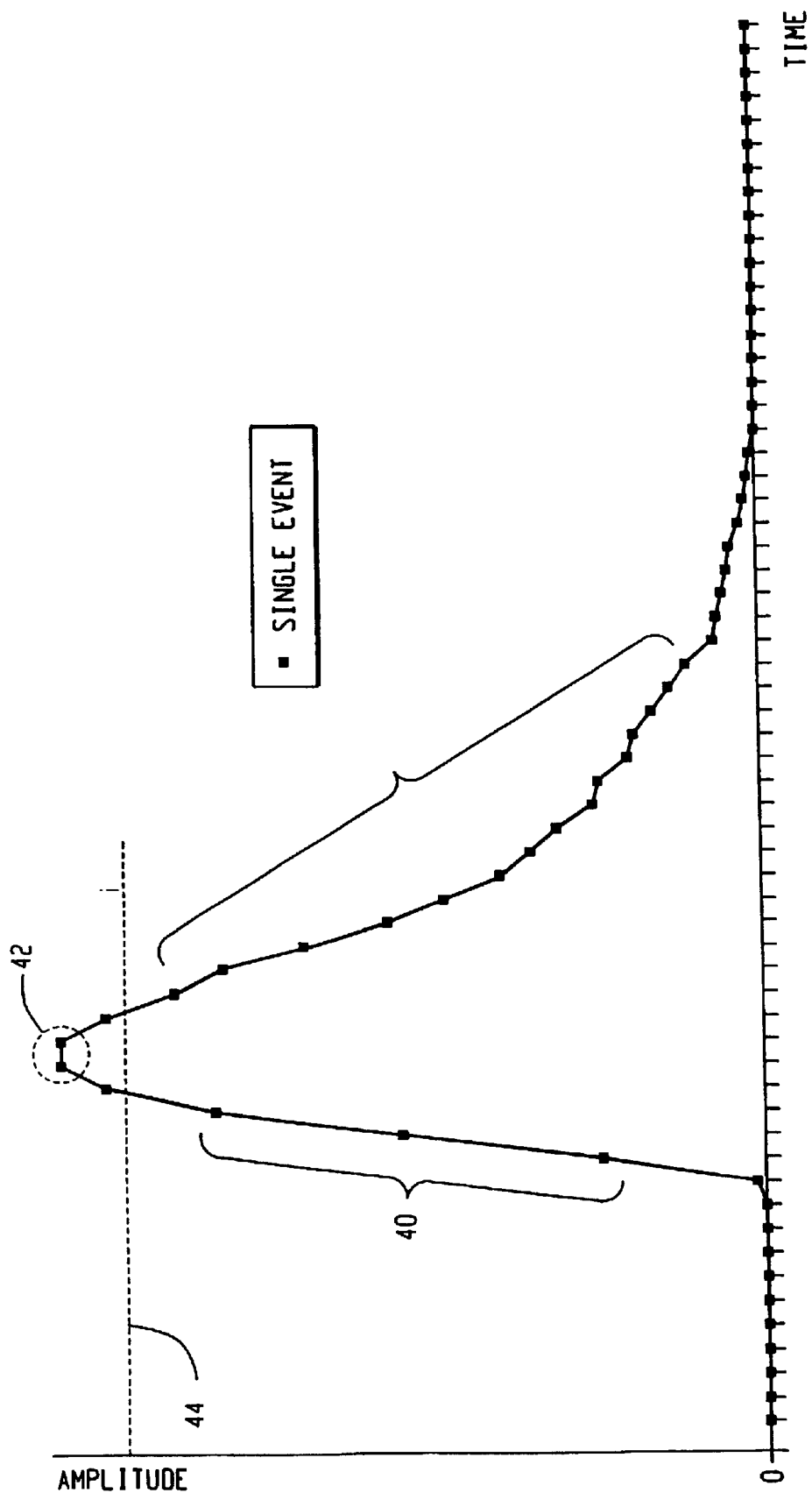
FIG. 5 illustrates a graphical depiction of an event in amplitude versus time.

Each of the sensors 22 generates a respective analog sensor output pulse (e.g., tube output pulse) in response to the received light flash. Furthermore, each of the sensors 22 is electrically connected to analog-to-digital converters 24. The analog-to-digital converters 24 convert the analog sensor output pulses to a series of digital sensor output values, as illustrated in FIG. 5. As is discussed in more detail below, a processor 26 determines coordinates in two dimensions of the location and the energy of the scintillation event that occurred in the crystal.

Figure 2:
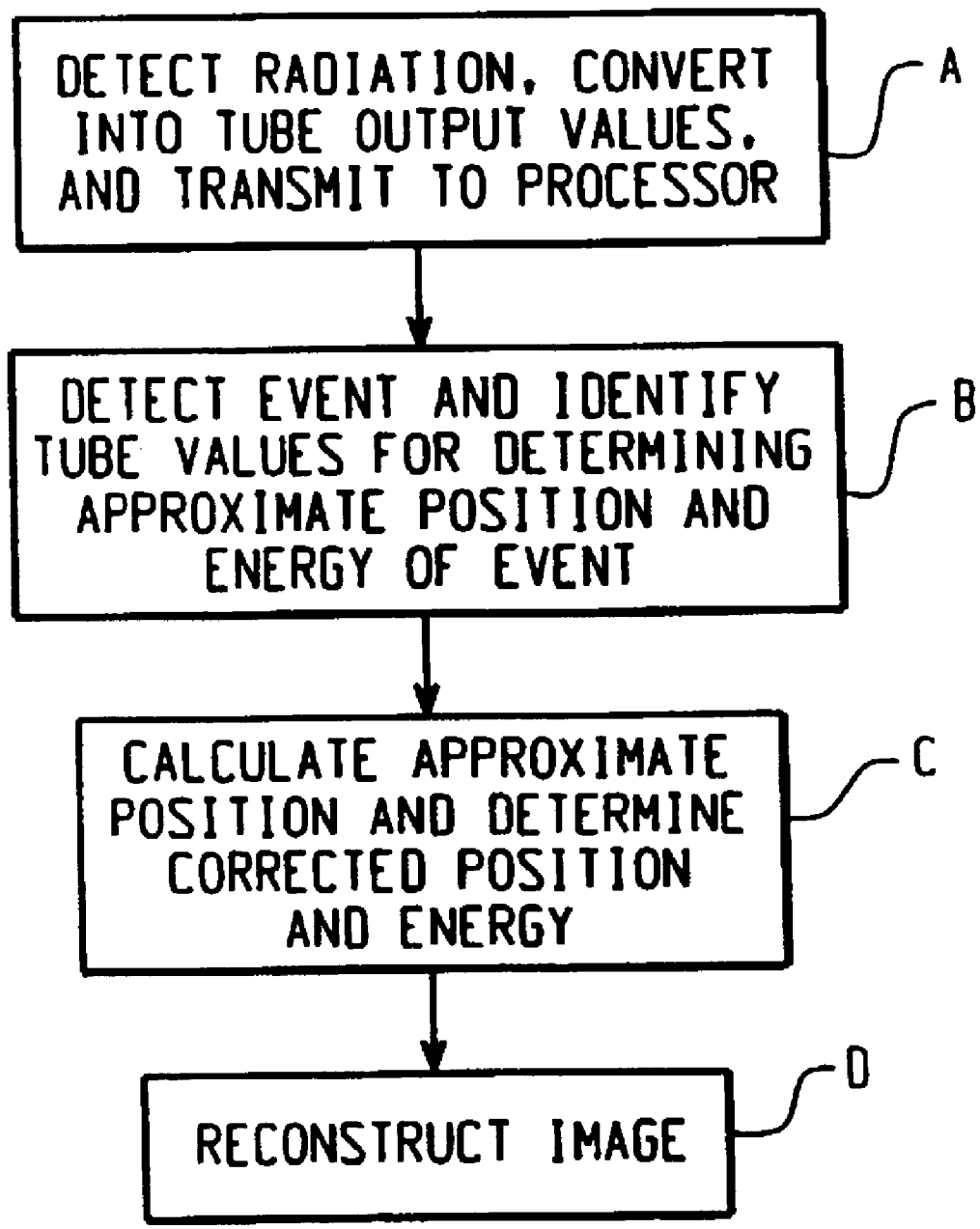
FIG. 2 illustrates an overview flowchart according to the present invention.

With reference to FIGS. 1 and 2, radiation is detected and converted into sensor output values (e.g., tube output values), which are transmitted to the processor 26 in a step A. Then, in a step B, the processor 26 detects that an event occurs and identifies which sensor values (e.g., tube values) will be used for determining an approximate position and energy of the event. In a step C, the processor 26 calculates the approximate position and energy of the event and then determines a corrected position by applying a weighting algorithm. Finally, in a step D, an image (e.g., volumetric image) is reconstructed.

Figure 3:
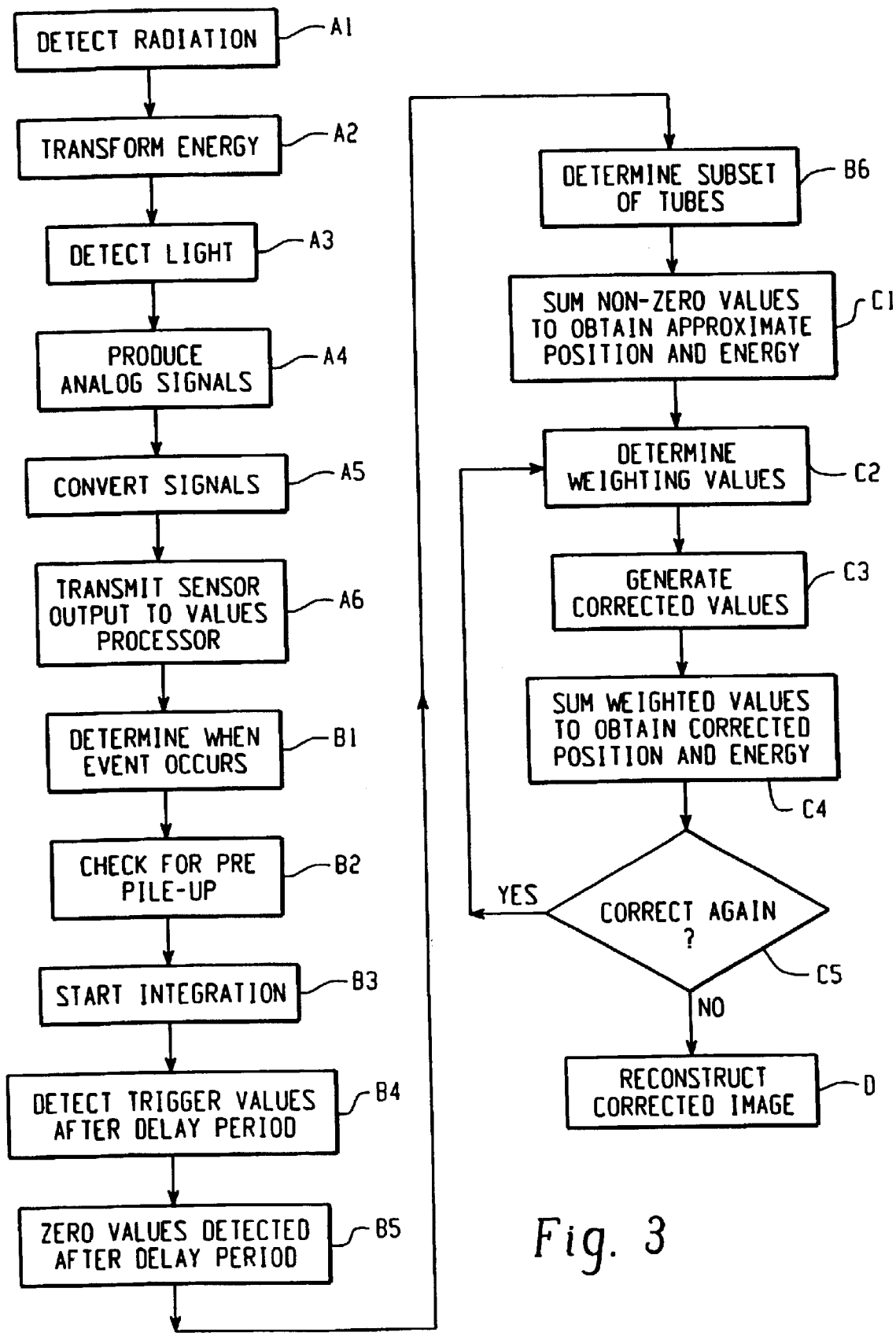
FIG. 3 illustrates a flow chart detailing the flowchart shown in FIG. 2.

With reference to FIGS. 2 and 3, each of the steps A–C includes a plurality of respective sub-steps, which are discussed below. For ease of explanation, each of the sub-steps is identified with a reference numeral specifying both the step (see FIG. 2) and the sub-step (see FIG. 3).

With reference to FIGS. 1–3, each radiation event is detected within the array of sensors 22 in a sub-step A1. The radiation produces gamma quanta that arise in the disintegration of radioisotopes. The disintegration quanta strike the scintillation crystal, which preferably includes doped sodium iodide (NaI) causing a scintillation. Light from the scintillation is distributed over a large number of the sensors 22.

Figure 4:
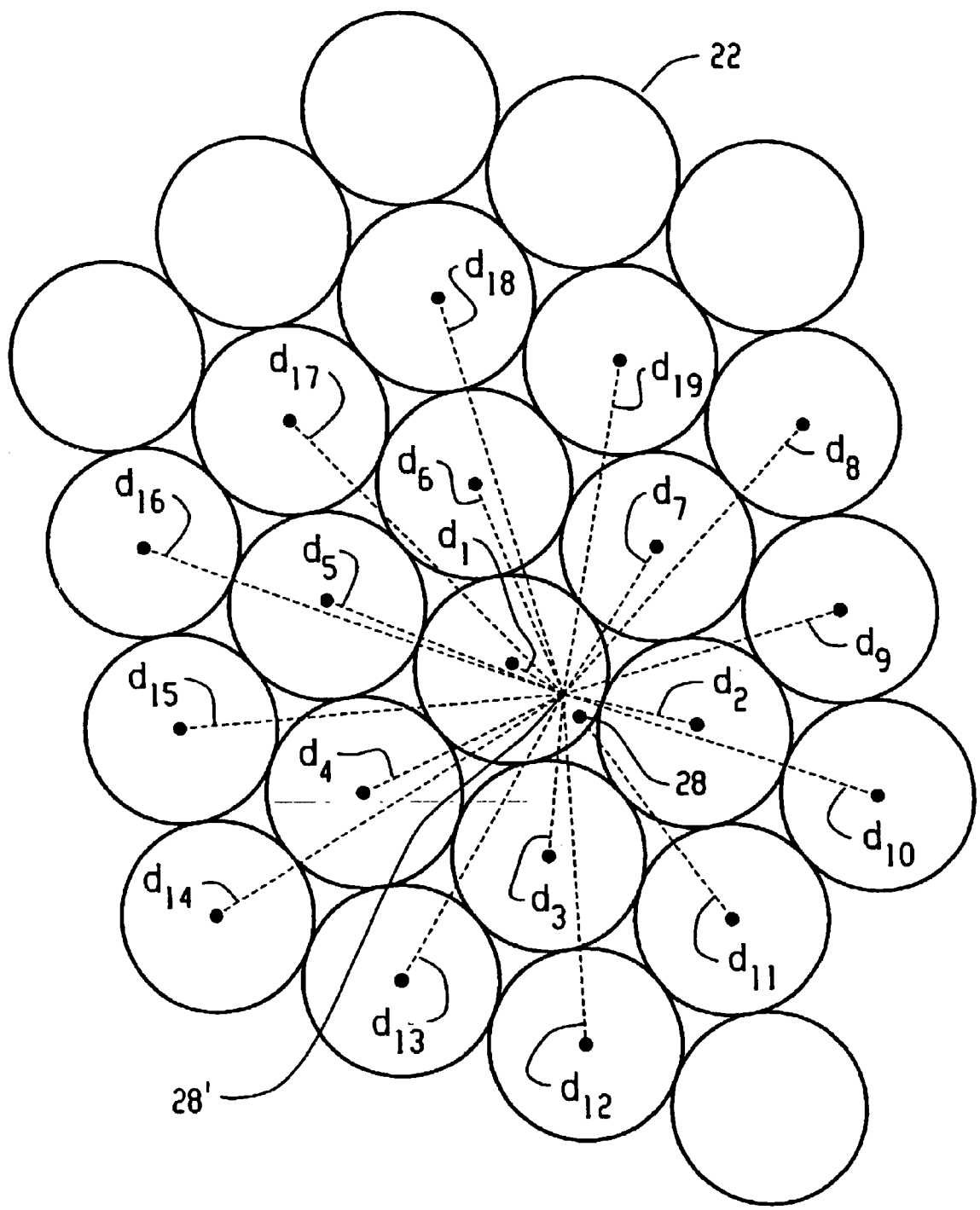
FIG. 4 illustrates a partial array of sensors.

As illustrated in FIG. 4, the scintillation, which is created by a radiation event, is illustrated centered at an arbitrary position 28. It is to be understood that only a partial array of the sensors 22 is shown in FIG. 4.

With reference to FIGS. 1, 3, and 4, the energy of the absorbed gamma quantum is converted, or transformed, into the flash of light at the position 28 by the scintillation crystal in a sub-step A2. The sensors 22 detect (receive) the scintillation light in a sub-step A3. Then, the sensors 22 produce the respective analog sensor output signals in a sub-step A4. The relative strengths of the analog sensor output signals are proportional to the respective amounts of the scintillation light received by the sensors 22 in the sub-step A3. The analog-to-digital converters 24 convert the analog sensor output signals to respective series of digital sensor output values in a sub-step A5. The digital sensor output values are then transmitted to the processor 26 in a sub-step A6.

Referring now to FIGS. 1 and 3–5, a scintillation event 28 typically includes a rapidly changing portion 40, which reaches a peak 42. The processor 26 detects that an event occurs (starts) in a sub-step B1 by analyzing the output values for each of the sensors. In the preferred embodiment, the processor 26 triggers (detects) that an event occurs when a sensor output value surpasses a trigger amplitude 44.

For the processor to determine the energy of the event 28, the area underneath the curve is determined. The signal is sampled at a rate sufficient to capture an appropriate number of amplitude values. A rate between 40 to 70 MHz provides a useful number of samples. Artisans appreciate with further reference to FIG. 5, that the integration or combination of sample data points is relatively straight-forward for a single scintillation event. The integration becomes problematic when several pulses overlap, a condition known as pile-up.

As discussed above, a post-pulse pile-up occurs when a subsequent event is detected during an integration period of the first event. A pre-pulse pile-up occurs when the processor 26 indicates the presence of a previous event that occurred before the current event that is being integrated. The processor 26 checks for a pre-pulse pile-up in a sub-step B2. In particular, the processor 26 checks whether the sensor outputs exceed a predetermined nominal or baseline value, which would exist in the absence of light. To avoid the undesirable effects of pulse pile-up, the integrated values of these sensors are zeroed (nulled).

The sensor output values are integrated, during an integration period, for each sensor in a sub-step B3. Subsequent triggers are detected after a delay period (post-pulse pile-up) (e.g., 75 nanoseconds), which begins substantially simultaneously when the integration period begins, in a sub-step B4. The integration values associated with the subsequent, post-pulse pile-up triggers are zeroed in a sub-step B5. It is assumed that all of the sensors 22 in the immediate vicinity of the first event 28 have already caused the trigger processor 26 to trigger within this delay period for the first event 28. If the baseline processor indicates the presence of a previous event (pre-pulse pile-up), the integrated value of the corresponding sensor is also zeroed (nulled).

It is noted that the subsequent scintillation events will introduce some error. More specifically, the sensors which see the subsequent scintillation events sufficiently strongly to reach the triggering threshold are zeroed (nulled). However, the peripheral sensors that only saw a small fraction of the light from the subsequent scintillation events still have their outputs incorporated into the summation, which determines the position or the energy of the first scintillation event 28. It is assumed, however, that the outputs from these peripheral sensors are small enough, when compared to the total summation, that the error they contribute is negligible.

In a sub-step B6, a subset of nineteen (19) sensors, including the sensor 22 having a maximum integrated value along with a group (e.g., 18) of nearest sensors, are selected. Then, in a sub-step C1, the processor determines the approximate position 28' and energy of the event 28 using the subset of nineteen (19) sensors within the array of sensors 22, preferably using weighted sums to determine a centroid (e.g., the Anger algorithm). Looking to the nineteen (19) sensors closest to the event $22_1, 22_2, 22_3, \ldots, 22_{19}$, it is assumed that the intensity of light received by each sensor is proportional to a corresponding distance $d_1, d_2, d_3, \ldots, d_{19}$, between the sensor and the event. This linear proportionality places the event at the point 28' in FIG. 4. If the sensor array were linear, point 28' would be an accurate estimate of the actual location 28 at which the event occurred. Due to inherent non-linearities, the point 28' is typically shifted from the actual event 28.

Figure 6:
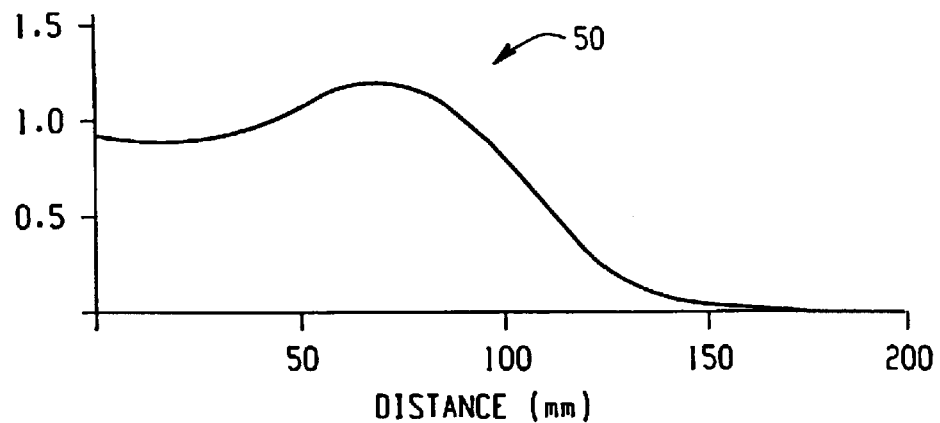
FIG. 6 illustrates an optimal weighting graph according to the present invention in multiplier correction value versus distance.

Then, in a sub-step C2, the processor 26 determines weighting (correcting) values as a function of the respective distances from the point 28' to the centers of the sensors 22, in the nineteen (19) sensor example, a weighting function for each of distances $d_1, d_2, \ldots, d_{19}$. In the preferred embodiment, the weighting values are assigned from an optimal weighting graph 50 as shown in FIG. 6. With reference to FIGS. 4–6, the graph 50 is designed by empirical measurement with sensors having a diameter of about 75 mm. However, it is to be understood that analogous graphs can be generated for sensors having other diameters. It is expected that graphs used for sensors having other diameters will have similar shapes to the graph 50. More specifically, the actual fall-off, i.e. amplitude of sensor output with distance from the center of the sensor, is measured. This actual fall-off is compared with the desired fall-off for a linear system. The deviation in the fall-off curves results in the weighting function of FIG. 6. That is, operating on the actual fall-off curve with the curve of FIG. 6 results in the desired ideal fall-off curve. Preferably, the curve of FIG. 6 is digitized and stored in a look-up table 52. Each of the distances $d_1, \ldots, d_{19}$ is addressed to the abscissa of the graph 50 so that a corresponding weighting factor is retrieved from the ordinate. Therefore, in the nineteen (19) sensor example, nineteen (19) weighting factors are retrieved from the ordinate. In this manner, the response of sensors beyond the closest seven (7) are also used in the calculation and a subset including nineteen (19) sensors is selected.

Figure 7:
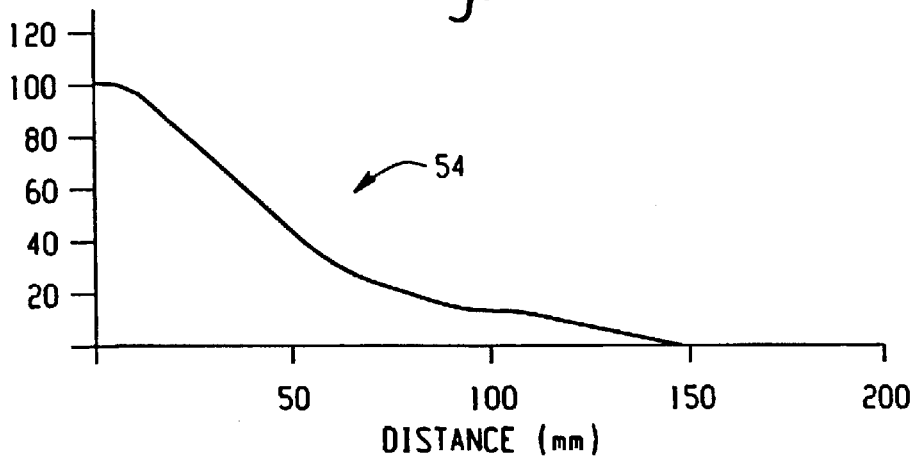
FIG. 7 illustrates an actual fall-off curve used for obtaining the optimal weighting graph of FIG. 6.
Figure 8:
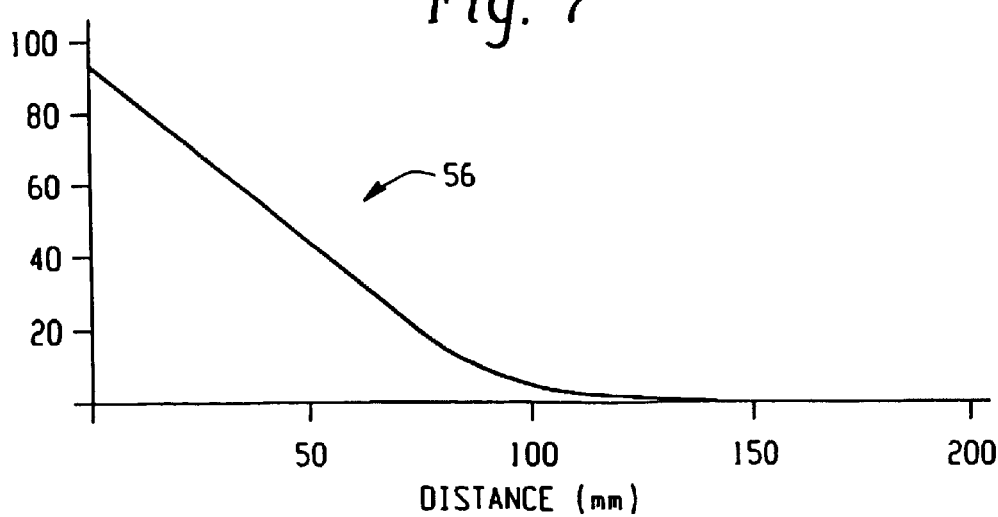
FIG. 8 illustrates a desired fall-off curve used for obtaining the optimal weighting graph of FIG. 6.

With reference to FIGS. 6–8, the graph 50 is generated as a function of an actual fall-off curve 54 (input response curve) and a desired fall-off curve 56 (desired response curve). More specifically, as will be discussed in more detail below, the graph 50 is obtained by dividing the desired response curve 56 by the input response curve 54. In other words, the weighting values are generated for each distance by dividing the desired response curve 56 by the input response curve 54 at each distance. The desired response curve 56 has the characteristic of smoothly reaching a zero (0) value at a distance chosen to include the appropriate number of sensors in the centroid. The desired curve 56 also has the characteristic of being substantially non-discontinuous and substantially linear. The input response curve is measured or modeled for a given camera geometry, which includes crystal thickness, glass thickness, sensor diameter, and any other operating conditions.

With reference again to FIGS. 1 and 3–5, in the sub-step C2 each of the distances $d_1$ through $d_{19}$, as well as the distances of further out sensors, are used for addressing the look-up table to determine corresponding weighting factors. In a sub-step C3, corrected sensor values are generated as a function of the weighting factors. It is to be understood that in other embodiments, the look-up table may also be indexed as a function of time, temperature, count-rate, depth of interaction, and/or event energy.

The processor 26 sums the weighted values in a sub-step C4 to determine the corrected position 28 and energy. A decision is made in a sub-step C5 whether to iterate (repeat) the correction process. If it is decided to repeat the process of correcting the event position, control is passed back to the sub-step C2 for determining subsequent weighting values from the look-up table based on the corrected position 28. Otherwise, control is passed to the step D for reconstructing the image.

The camera illustrated in FIG. 1 has a SPECT mode and a PET mode. In the SPECT mode, the heads have collimators which limit receipt of radiation to preselected directions, i.e., along known rays. Thus, the determined location on the crystal 20 at which radiation is detected and the angular position of the head define the ray along which each radiation event occurred. These ray trajectories and head angular position from an angular position resolver 60 are conveyed to a reconstruction processor 62 which back projects or otherwise reconstructs the rays into a volumetric image representation in an image memory 64.

In a PET mode, the collimators are removed. Thus, the location of a single scintillation event does not define a ray. However, the radioisotopes used in PET scanning undergo an annihilation event in which two photons of radiation are emitted simultaneously in diametrically opposed directions, i.e., 180° apart. A coincidence detector 66 detects when scintillations on two heads occur simultaneously. The locations of the two simultaneous scintillations define the end points of a ray through the annihilation event. A ray or trajectory calculator 68 calculates the corresponding ray through the subject from each pair of simultaneously received scintillation events. The ray trajectories form the ray calculator 68 are conveyed to the reconstruction processor for reconstruction into a volumetric image representation.

A video processor 70 processes the image representation data for display on a monitor 72.

The processor 26 also determines an energy of the event 28 by integrating, or summing, the corrected sensor output values during an integration period. The integration period preferably lasts about 250 nanoseconds, although the integration period may vary in different scintillation crystals, radiation energies, or software applications. That is, once all of the integrated sensor outputs of FIG. 5 corresponding to the event are scaled by the correction curve 50, they are summed to determine the energy of the event.

Stated in mathematical terms, the energy E of the event 28 and the position x of the event 28 are calculated as:

$$E = \sum_i w_i^E S_i,$$

and $$x = \frac{\sum_i w_i^x S_i x_i}{\sum_i w_i^x S_i},$$

where $x_i$ represents respective sensor locations, $S_i$ represents the respective sensor output values, $w_i^E$ represents energy weighting values, and $w_i^x$ represents distance weighting values.

In one embodiment, $w_i^E$ and $w_i^x$ are a function of the respective distance $|x_i-x_0|$ between the sensor location $x_i$ and the initial determined position $x_0$ 28' of the event 28 (see FIG. 6). As discussed above, the initial position $x_0$ is determined as a centroid of the event 28. Since a detector normally consists of photomultiplier sensors arranged in a two-dimensional array, calculation of the distance usually involves computing the value of the difference between the sensor location $x_i$ and $x_0$ for each of a plurality of coordinates. The differences are squared, summed, and the square root is taken to find $d_i$. In order to avoid the complexities of taking the square root, a table look-up may be used. Alternatively, a two-dimensional fall-off correction curve table and/or two-dimensional pre-correction table can be indexed by the absolute values of the differences between the sensor location $x_i$ and $x_0$ in order to save the step of calculating the distance directly.

As will be discussed in more detail below, the weighting values $w_i^x$ are optionally pre-corrected as a function of the energy being imaged.

Figure 9:
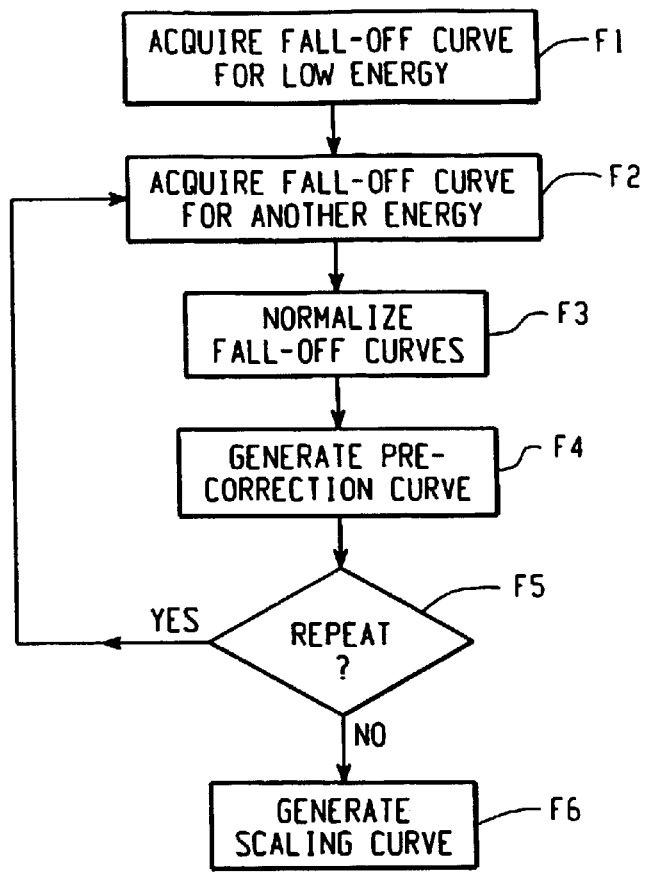
FIG. 9 illustrates a flowchart for generating a scaling curve according to the present invention.
Figure 10:
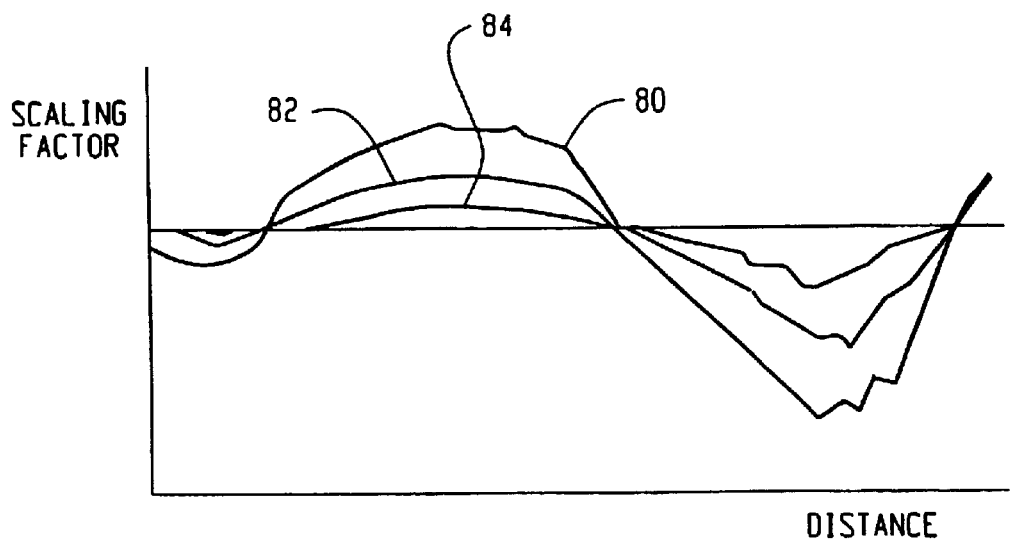
FIG. 10 illustrates various energy ratio curves according to the present invention.
Figure 11:
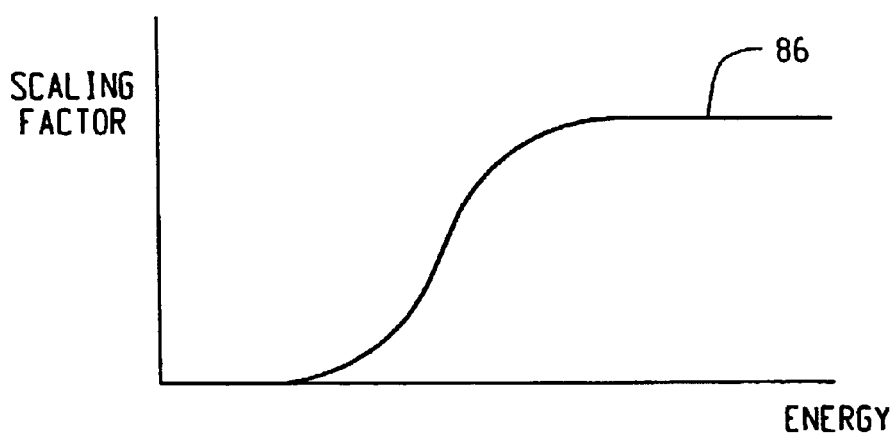
FIG. 11 illustrates an energy scaling curve according to the present invention.
Figure 12:
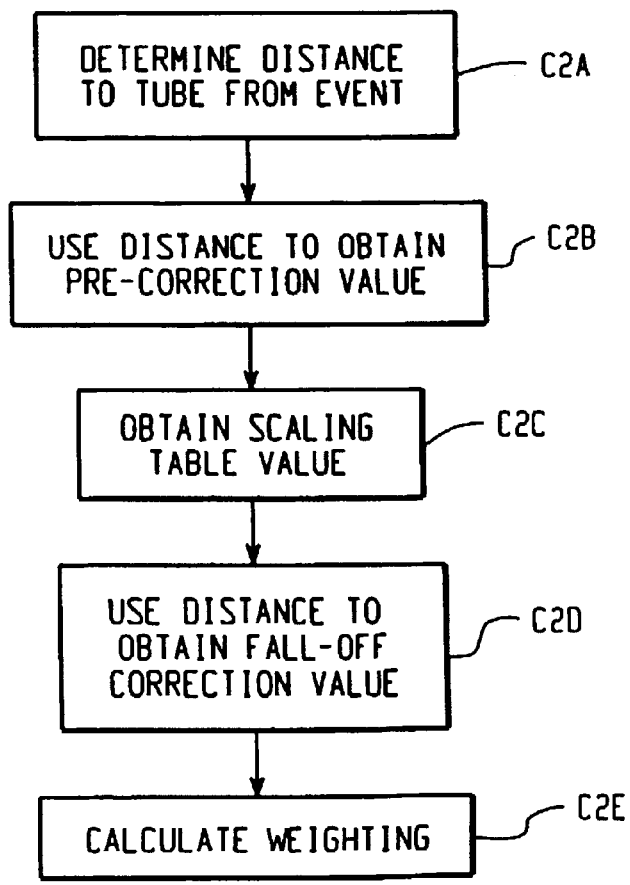
FIG. 12 illustrates a flow chart detailing the flowchart shown in FIG. 3.

With reference to FIGS. 9–11, a representative fall-off curve for one energy level E1 is generated in a step F1. Preferably, the energy level E1 is a low energy within a range including 75 KeV and 511 KeV (e.g., about 75 KeV). For purposes of explanation, it is to be understood that the curve 54 represents the actual fall-off curve for the energy E1. A fall-off curve (not shown) for another energy E2, E3, E4 is acquired in a step F2. The fall-off curve (including, for example, the fall-off curve 54 for the energy level El) is normalized to be within a range including, for example, zero (0) and 100 in a step F3. The fall-off curve for one of the energies E2, E3, E4 is divided by the fall-off curve 54 for the first energy E1 in a step F4, thereby generating one of a plurality of energy ratio curves (pre-correction curves) 80, 82, 84 (see FIG. 10). The energy ratio curves 80, 82, 84 represent weighting that must be applied as a function of distance to a sensor's output when a respective one of the energies E2, E3, E4 is being imaged.

A decision is made in a step F5 whether to repeat the process of generating another one of the energy ratio curves 80, 82, 84. If it is desired to repeat the process, control returns to the step F2 for acquiring the fall-off curve for another energy. Otherwise, control passes to a step F6. With reference to FIG. 10, the energy ratio curve 80 represents E1/E2, the energy ratio curve 82 represents E1/E3, and the energy ratio curve 84 represents E1/E4. Although only four (4) energy levels are discussed, it is to be understood that any number of energy levels may be generated. It is noted that each of the energy ratio curves 80, 82, 84 may be made smoother by collecting more data and/or applying commonly known regression or curve fits.

It is evident that all of the energy ratio curves 80, 82, 84 generally have a same shape but are scaled differently. Since table space (i.e., computer memory) is usually limited due to memory size in practical implementations and/or time constraints prohibit acquiring curves for all continuous energies, an additional energy scaling curve may optionally be used.

An energy scaling curve 86 is generated by determining scaling values between the energy ratio curve 80, which represents E1/E2 (e.g., the highest energy) and each of the energy ratio curves 82, 84, which represent E1/E3 and E1/E4, respectively. In this manner, the energy scaling curve 86, which yields an energy scaling factor as a function of energy, is produced in the step F6. It is to be understood that standard methods are used for fitting a curve to the scaling values between the various energy ratio curves. As will be discussed in more detail below, a scaling value $sv_i$ may be obtained from the energy scaling curve 86 as a function of energy.

In the current example, it is assumed that the optimal weighting graph 50 (see FIG. 6) is calibrated for the energy E1. Therefore, once the energy ratio curves 80, 82, 84 are created, the optimal weighting graph 50 (see FIG. 6) may optionally be "pre-corrected" as a function of an energy ratio curve corresponding to the energy being imaged and a distance of the sensor. More specifically, with reference to FIGS. 3 and 10–12, a distance between a sensor center and the event 28 is determined in a sub-step C2A. Then, in a sub-step C2B, an energy pre-correction factor $pv_i$ is optionally obtained from the graph 80 as a function of the distance determined in the sub-step C2A. Importantly, an appropriate one of the energy ratio curves 80, 82, 84 is selected as a function of the energy being imaged. A scaling value $sv_i$ is optionally obtained from the energy scaling curve 86 in a sub-step C2C.

A fall-off correction value $fcv_i$ is obtained from the optimal weighting graph 50 as a function of distance in a sub-step C2D. The weighting factor $w_i^x$ is calculated in a sub-step C2E as $w_i^x=sv_i*pv_i*fcv_i$. Then, a corrected sensor output value is calculated as $S_i^x=w_i^x*S_i$ in the sub-step C3. The weighting factor $w_i^x$ and corrected sensor output value $S_i^x$ are used in the above equations for energy E and position x.

In the preferred embodiment, the fall-off curves for the energies E1, E2, E3, E4 (see, e.g., the fall-off curve 54 of FIG. 6), are generated by flooding an open detector with a radiation source of a known energy. For each event that interacts in the crystal of the detector, an estimate of the event position is determined. Then, the distance from the event to each of the sensor centers is calculated. In order to have a statistically significant number of counts for each distance, multiple events are produced. A histogram of each sensor's output is created as a function of distance. It is to be understood that the resolution of the distances may be set according to a required application (e.g., ¼ of an intrinsic resolution of a gamma camera). The histograms from different sensor outputs may be combined to generate a composite histogram for the entire detector or certain areas that can naturally be grouped together. The mean value of each histogram is then computed to generate the fall-off curve as a function of distance. The curve can be normalized by dividing each value by the maximum fall-off value (e.g., the value at, the distance zero (0)).

Figure 13:
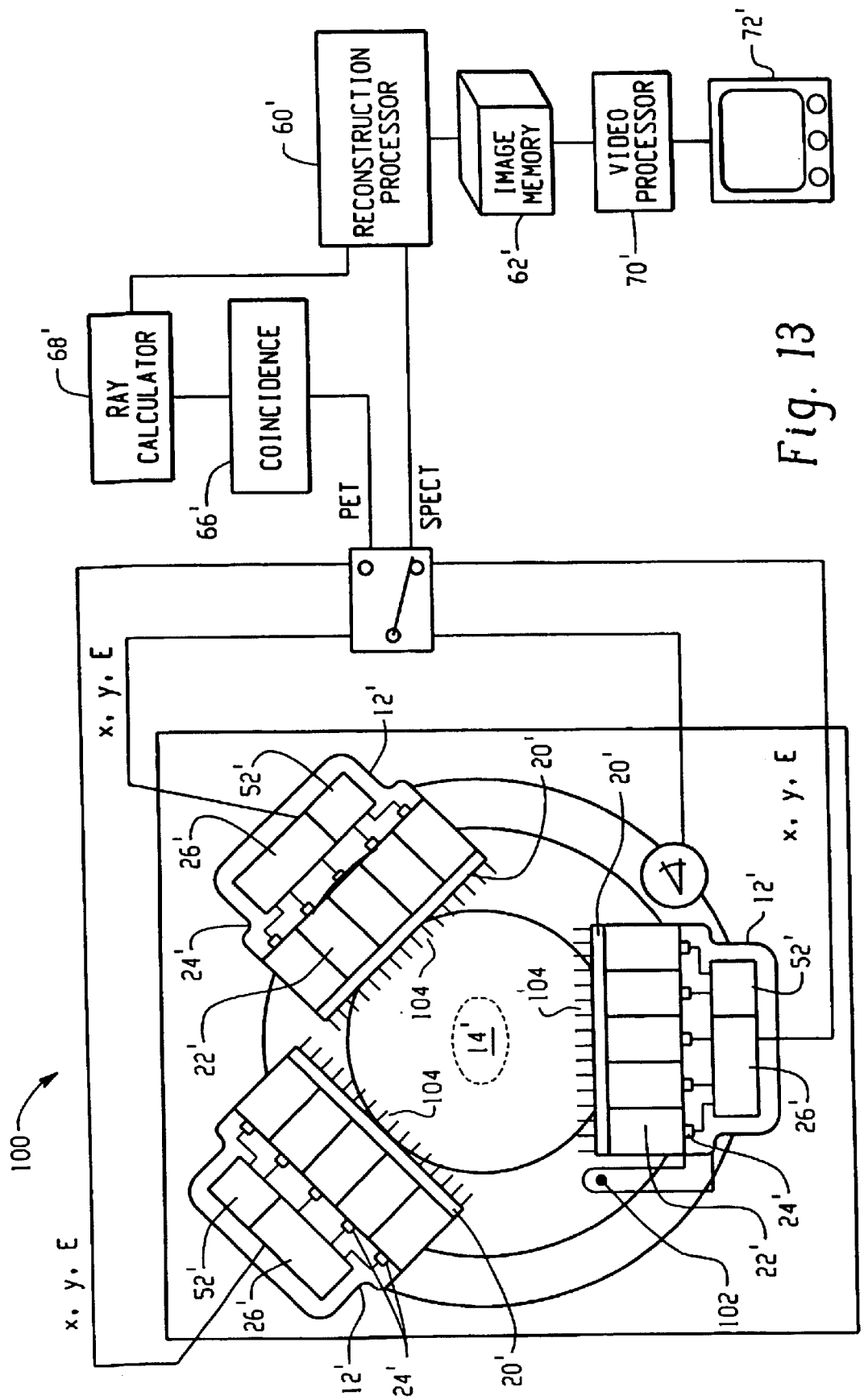
FIG. 13 illustrates an embodiment of the present invention including a PET scanner.

FIG. 13 illustrates a second embodiment of the present invention including single photon emission computed tomography ("SPECT") scanner. For ease of understanding this embodiment of the present invention, like components are designated by like numerals with a primed (') suffix and new components are designated by new numerals.

With reference to FIG. 13, a SPECT scanner 100 includes three (3) detectors 12' mounted for movement around a subject 14' in an examination region 16'. The subject is injected with a radioisotope. Each of the detectors 12' includes a scintillation crystal 20' for converting radiation events from the injected isotope into a flash of light energy or scintillation. Optionally, a radiation source 102 produces a fan of transmission radiation of a different energy than the injected radiation. Collimators 104 on the detectors limit and define the patches or rays along which each detector can receive emission and transmission radiation. The location of the scintillation and the position of the receiving detector uniquely determine the ray.

An array of sensors 22', e.g. 59 sensors, is arranged to receive the light flashes from the scintillation crystal 20'. Each of the sensors 22' generates a respective analog sensor output pulse (FIG. 5) in response to the received light flash. Furthermore, each of the sensors 22' is electrically connected to at least one of a plurality of analog-to-digital converters 24'. As discussed above, the analog-to-digital converters 24' convert the analog sensor output pulses to respective series of three digital sensor output values. Also, a processor 26' determines the energy and the location in two dimensions of each scintillation on the face of the detector, hence the ray along which the radiation originated. Additionally, the curves of FIGS. 6, 10, and optionally 11 are digitized and stored in respective look-up tables 52'.

Once the corrected position and energy are determined on a detector 12' at which a scintillation occurred and from the respective positions of the detectors, a processor 60' reconstructs an image representation from the emission-data. When a radiation source 102 is used, the transmission data is used to correct the emission data for an improved image. The image representation is stored in an image memory 62'. A video processor 70' processes the image representation data for display on a monitor 72'.

Again, the three heads can be used without collimators in a PET mode. The heads are positioned to provide uniform coverage of the region of interest during annihilation events. A coincidence detector 66' determines concurrent events and a ray calculator 68' calculates the trajectory between each pair of coincident events.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A nuclear camera system comprising:
a detector for receiving radiation from a subject in an exam region, the detector including:
a scintillation crystal that converts radiation events into flashes of light;
an array of sensors arranged to receive the light flashes from the scintillation crystal, a plurality of the sensors generating a respective sensor output value in response to each received light flash; and
a processor that analyzes the sensor output values for detecting a start of the event, determines (a) an initial position and an energy of each of the detected radiation events (b) respective distances from the initial position of the detected event to the sensors, and (c) a corrected position and energy of each detected radiation event in accordance with weighing values which are generated based on the respective distances from the determined initial position of each detected event to the sensors, and generates an image representation from the corrected positions and the energies.

2. The nuclear camera system as set forth in claim 1, wherein the processor analyzes the sensor output values for detecting a previous event, any sensor output values associated with the previous event being excluded from calculations of an initial position and an energy of a next detected event.

3. A nuclear camera system including:
a detector for receiving radiation from a subject in an examination region, the detector including:
a scintillation crystal that converts radiation events into a plurality of light flashes,
a plurality of analog sensors arranged to receive each light flash from the scintillation crystal, the plurality of analog sensors generating respective analog output values in response to each received light flash, and
a plurality of analog to digital converters, each of the analog sensors being electrically connected to an associated one of the analog to digital converters for converting each of the analog output values to an individual sensor digital output values; and
a processor to analyze the individual sensor digital output values for detecting a start of the event, integrating the digital output values from the start of the event over an integration period, and calculating an initial position and energy of each detected radiation event in response to detecting a next event with one of the sensors after the integration period of the event begins, excluding the sensor digital output values of the one sensor associated with the next event from calculations of the initial position and the energy of the event, the processor further generating a corrected position and energy from the initial position and energy and generating an image representation from a plurality of the corrected positions and energies.

4. A nuclear camera system comprising:
a detector for receiving radiation from a subject in an exam region, the detector including:
a scintillation crystal that converts radiation events into flashes of light;
an array of analog sensors arranged to receive the light flashes from the scintillation crystal, a plurality of the analog sensors generating respective analog sensor output values in response to each received light flash; and
a plurality of analog to digital converters, each of the analog sensors being electrically connected to an associated analog to digital converter for converting the analog sensor output values to a series of digital numbers; and
a processor which (i) detects overlapping events that are sufficiently temporally close such that their light flashes are at least partially concurrent, (ii) determines at least one of position and energy of at least one of the overlapping events while compensating for the partially concurrent light flash of the other, and (iii) generates an image representation from the initial positions and the energies.

5. The nuclear camera system as set forth in claim 4, wherein the processor analyzes the sensor output values for detecting a start of each detected event.

6. The nuclear camera system as set forth in claim 5, wherein the processor analyzes the sensor digital number for detecting an ongoing previous event and excludes any sensor digital numbers associated with the previous event from calculations of an initial position and an energy of a the detected event.

7. The nuclear camera system as set forth in claim 5, wherein in response to the processor detecting another event after an integration period of one event begins, the sensor digital numbers associated with the another event are nulled from calculations of the initial position and the energy of the one event.

8. The nuclear camera system as set forth in claim 4, further including:
   second detector disposed across an imaging region from the first detector;
   a coincidence detector connected with the first and second detectors for detecting concurrent events on both detectors; and
   a reconstruction processor for determining rays through the imaging region between concurrent events and reconstructing the rays into an output image representation.

9. A method of generating an image representation comprising:
   converting radiation from a subject in an examination region into flashes of light;
   receiving the flashes of light with an array of sensors;
   generating respective sensor output values in response to each received light flash;
   analyzing the sensor output values to detect a start of each flash of light;
   determining for each flash of light (i) an initial position and an energy and (ii) distances from the determined initial position to each sensor which received the flash of light;
   determining weighting values for each sensor based on the determined distances;
   correcting each initial position in accordance with the determined weighting values; and
   generating an image representation from the corrected positions.

10. The method of generating an image representation as set forth in claim 9, further including:
    analyzing the sensor output values for detecting a previous flash; and
    in the step of determining at least one of the initial position and the energy, ignoring any of the sensor output values associated with the previous flash.

11. The method of generating an image representation as set forth in claim 9, further including:
    in response to detecting a subsequent flash after an integration period of one of the light flashes begins, ignoring the sensor values associated with the sensors receiving the subsequent flash when calculating the initial position and the energy of the light flash.

12. A method of generating an image representation from detected radiation events, the method comprising:
    converting radiation from a subject in an examination region into flashes of light;
    receiving the flashes of light with an array of sensors;
    generating respective sensor output values in response to each received light flash;
    detecting temporally adjacent light flashes that are at least partially overlapping;
    determining a position for each non-overlapping flash of light;
    excluding the sensor output values that are responsive to two or more of the overlapping light flashes, when determining the position of each non-overlapping flash of light; and,
    generating an image representation from the determined positions.

13. The method of generating an image representation as set forth in claim 12 further including:
    detecting a start of the each flash of light.

14. The method as set forth in claim 9 wherein the step of determining weighting values includes:
    generating a plurality of fall-off curves, each of the fall-off curves corresponding to a respective one of a plurality of energies;
    creating a plurality of energy ratio curves as a function of the fall-off curves, each of the energy ratio curves representing a relationship between a selected pairs of the energies;
    determining a weighting value from one of the energy ratio curves for scaling the fall-off curve associated with one of the energies; and the step of correcting includes:
       correcting the at least one of the initially determined position and the initially determined energy as a function of the weighting value and the fall-off curve associated with the initially determined energy.

15. The method as set forth in claim 14, further including generating an energy scaling curve representing a relationship between the energy ratio curves, the determining step also determining the weighting value as a function of the energy scaling curve.

16. The method as set forth in claim 14, wherein the step of generating each of the fall-off curves includes:
    dividing a selected fall-off curve by an actual fall-off curve, each of the fall-off curves representing an energy amplitude as a function of distance.

17. The method as set forth in claim 14, further including before the creating step, normalizing the fall-off curves.

* * * * *